US00PP14087P39

(12) United States Plant Patent
Lighty et al.

(10) Patent No.: US PP14,087 P3
(45) Date of Patent: Aug. 19, 2003

(54) TIARELLA PLANT NAMED 'SPRINGWOOD'

(75) Inventors: Stephen K. Lighty, Cochranville, PA (US); Angela J. Treadwell, Baltimore, MD (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 09/875,926

(22) Filed: Jun. 8, 2001

(65) Prior Publication Data

US 2002/0199226 P1 Dec. 26, 2002

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Burns, Doane, Swecker & Mathis, LLP

(57) ABSTRACT

A new variety of *Tiarella cordifolia* var. *collina* plant is provided that is well suited for growing as a distinctive ground cover. The new variety exhibits a compact mounding clump growth habit with the substantial absence of runners. Attractive white flowers are formed on unbranched flower stalks. The lobed leaves are ovate in configuration and possess a matte finish. During the summer the leaves are green and bear somewhat maroon centers. During the fall, the leaves assume a red coloration of variable intensity. The available choices of ornamental ground covers are expanded.

2 Drawing Sheets

Botanical/commercial classification: *Tiarella cordifolia*/ Tiarella Plant.
Varietal denomination: cv. 'Springwood'.

SUMMARY OF THE INVENTION

The new *Tiarella cordifolia* var. *collina* variety was discovered during 1996 as a found seedling in the garden of Richard W. Lighty at Kennett Square, Pa., U.S.A. The exact parentage of the new variety is unknown. A variable population of the species was growing nearby that included *Tiarella cordifolia, Tiarella cordifolia* var. *collina*, and *Tiarella cordifolia Wherryi*. Some or all of these plants are likely included in the parentage of the new variety of the present invention.

The new variety has been carefully preserved and studied since the time of its discovery. Had such new variety not been discovered and preserved, it would have been lost to mankind.

It was found that the new *Tiarella cordifolia*, var. *collina* variety of the present invention exhibits the following combination of characteristics:

(a) exhibits a compact mounding clump growth habit with the substantial absence of runners, (b) forms attractive white flowers on unbranched flower stalks, (c) forms lobed ovate green leaves having a matte finish during the summer that bear somewhat maroon centers and turn red of variable intensity during the fall, and (d) is particularly well suited for growing as a distinctive ornamental ground cover.

The new variety of the present invention can be readily distinguished from other previously known varieties of the species in view of the distinctive combination of characteristics discussed herein. The red fall color is considered to be particularly noteworthy.

The new variety well meets the needs of the horticultural industry and expands the choices of ornamental ground covers. It performs well wherever a ground cover is desired, and is particularly well suited for use as a border planting, use in shaded areas, and inclusion in a rock garden.

The division of clumps has been used to asexually propagate the new variety at West Grove, Pa., U.S.A. It has been found that the distinctive combination of characteristics of the new variety is firmly fixed and is reliably transmitted to succeeding generations. During observations to date, the new variety has been found to be readily amenable to such propagation.

The new variety has been named 'Springwood'.

BRIEF DESCRIPTION OF THE PHOTOGRAPHS

The accompanying photographs show typical plants of the new variety in color as nearly true as is reasonably possible to make the same in color illustrations of this character. The plants were approximately two years of age and were being grown outdoors on their own roots at West Grove, Pa., U.S.A.

DETAILED DESCRIPTION

Figure 1:
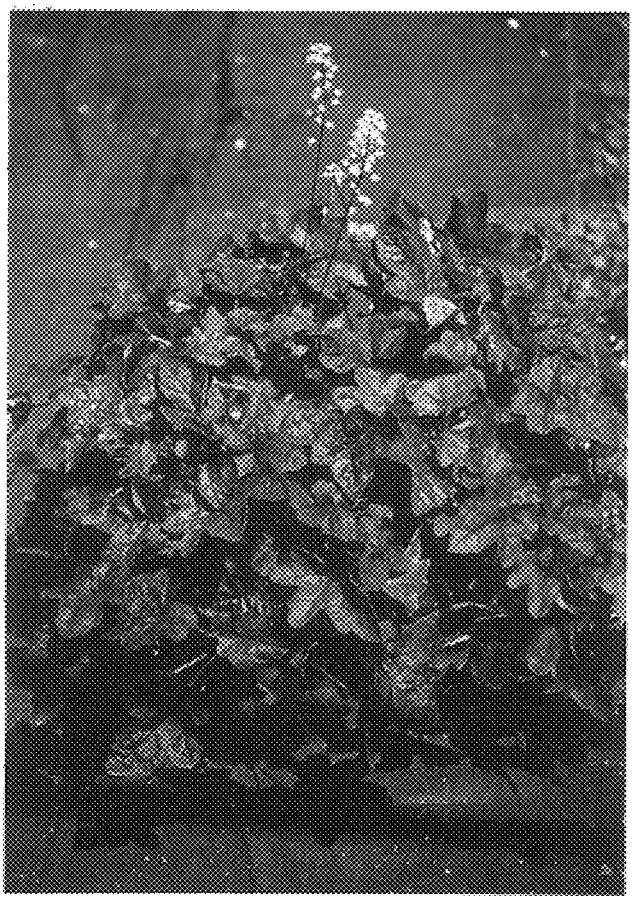
FIG. 1 illustrates a typical overall plant of the new variety while flowering during the summer. The commonly displayed maroon centers of the foliage are not readily depicted in the photograph.
Figure 2:
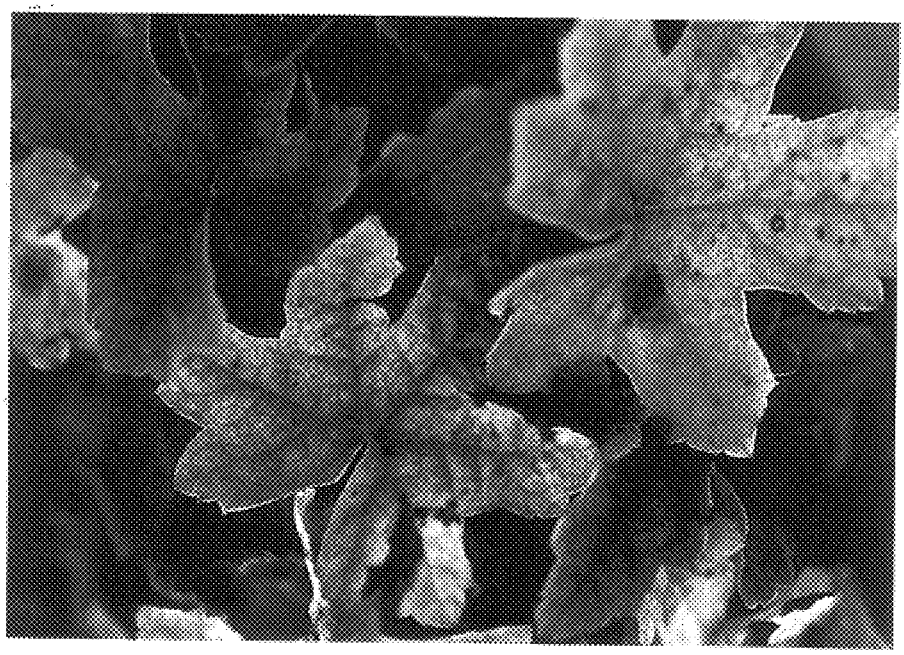
FIG. 2 illustrates the typical red coloration of the leaves having variable intensity that is displayed during the fall.
Figure 3:
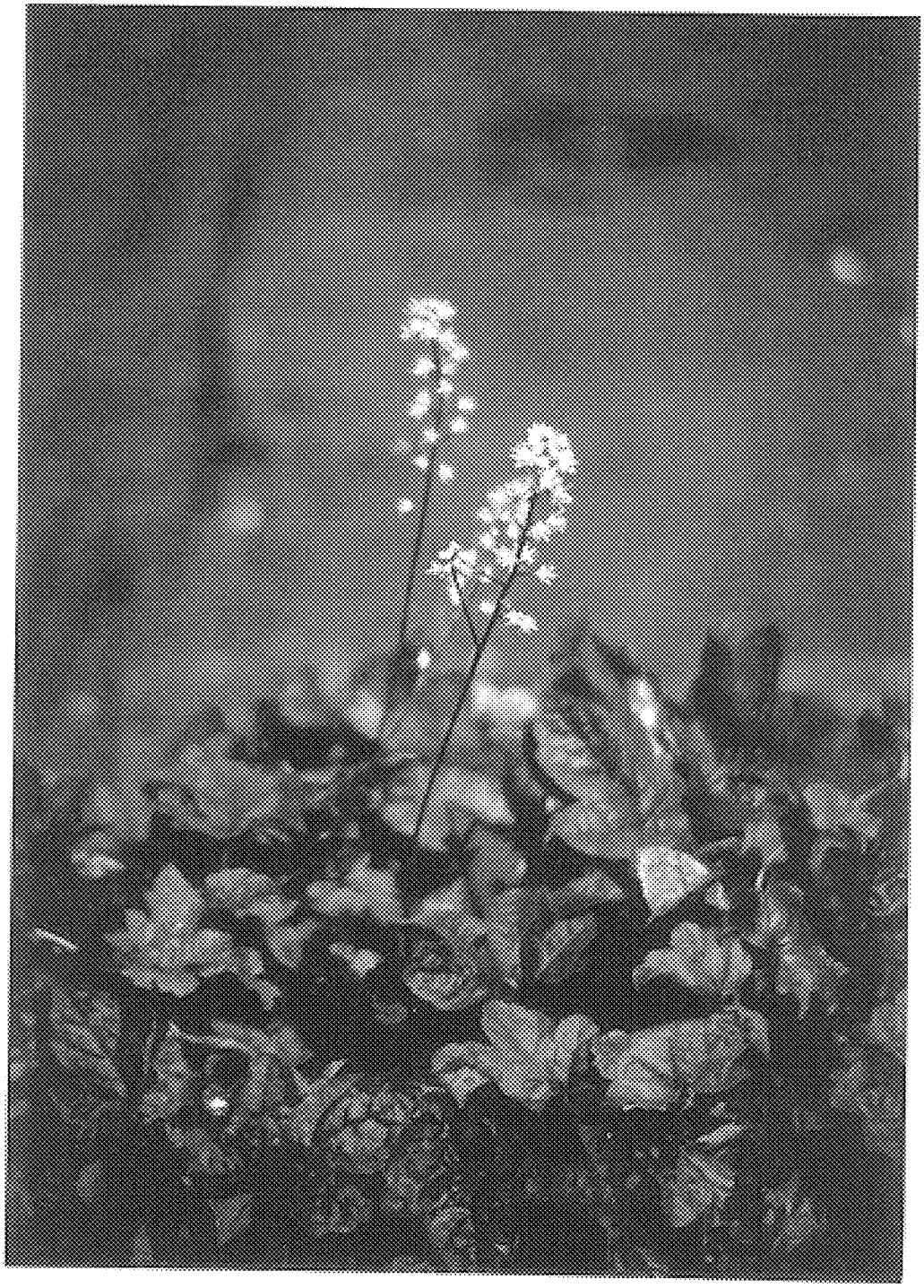
FIG. 3 illustrates a closer view of flowers and foliage during the summer. The commonly displayed maroon centers of the foliage are not readily depicted in the photograph.

The following is a detailed description of the new variety that was obtained while observing plants being grown outdoors during the summer and fall at West Grove, Pa., U.S.A. The plants were approximately two years of age and were being grown on their own roots. The chart used in the identification of color is The R.H.S. Colour Chart of The Royal Horticultural Society, London, England. More common color terms are to be accorded their ordinary dictionary significance.

Botanical classification: *Tiarella cordifolia,* var. *collina,* cv. 'Springwood'.

Plant:

*Habit.*—Compact mounding clump.

*Type.*—Evergreen.

*Height.*—Approximately 15 to 20 cm without blooms, and approximately 25 to 30 cm with blooms.

*Width.*—Approximately 30 cm.

Foliage:

*Type.*—Simple.

*Shape.*—Ovate to broadly ovate, palmately five-lobed (rarely seven-lobed) with an elongated central lobe, and irregularly crenate margins on all lobes having apiculate teeth. Each tooth has a small point which is relatively firm and consists of both a vein termination and the leaf blade.

*Length.*—Approximately 5.5 to 9.5 cm.

*Width.*—Approximately 5 7 cm.

*Margins.*—Incised with dentation.

*Apex.*—The lobes are broadly obtuse to rounded and cuspidate.

*Base.*—Cordate.

*Texture.*—Slightly rugose with a velvet matte finish.

*Arrangement.*—Basal clump.

*Venation.*—Palmately reticulate.

*Color.*—Young Foliage: On the dorsal surface Yellow-Green Group 144A to 144B, and Greyed-Purple Group 187A at the center and along the main vein, and on the ventral surface Yellow-Green Group 146B to 146C. Adult Foliage: On the dorsal surface Green Group 137B to 137D, and Brown Group 200B at the center and along the main vein, and on the ventral surface Yellow-Green Group 146B to Greyed-Green Group 191A. Fall Foliage: Both the ventral leaf surface (upper) and the dorsal leaf surface (lower) are characterized by areas of light red and darker reddish-purple that are near and through the following colors: Red Group 49D and Red-Purple Group 62D in the lighter areas to Red Group 53D and Greyed-Purple Group 186B in the mid-tones to Greyed-Purple Group 187A and 187B in the darker areas. The dorsal leaf surface exhibits a slightly glossier appearance when compared to the more matte appearance of the ventral leaf surface that commonly is expressed in the autumn foliage.

*Petiole.*—The length commonly varies from approximately 10 to 20 cm, and the diameter commonly is approximately 1.6 mm.

Inflorescence:

*Type.*—Raceme and perfect (bisexual).

*Number.*—Approximately 25 to 50 blooms per raceme.

*Bearing.*—On an unbranched stalk commonly having a height of approximately 25 to 30 cm.

*Calyx.*—Five-lobed.

*Petals.*—Five.

*Petal shape.*—Triangular and clawed.

*Stamens.*—Ten.

*Pistil.*—One.

*Flower size.*—Approximately 4 to 5 mm on average per floret.

*Color.*—On the dorsal surface White Group 155B and on the ventral surface White Group 155A.

*Fragrance.*—Slight and sweet.

*Pedicel.*—Approximately 4 mm in length on average.

Development:

*Vegetation.*—Clump-forming.

*Blooming.*—Abundantly when initially blooms during May/June and sporadically thereafter during the summer and fall.

*Resistance to disease.*—No susceptibility to diseases has been noted during observations to date.

*Hardiness.*—Has proven to grow well in U.S.D.A. Hardiness Zone No. 5.

*Propensity to form fruit/seeds.*—None observed to date.

Plants of the new 'Springwood' variety have not been observed under all possible environmental conditions to date. Accordingly, it is possible that the phenotype expression may vary somewhat with changes in light intensity and duration, cultural practices, and other environmental conditions.

I claim:

1. A new and distinct variety of *Tiarella cordifolia* var. *collina* plant having the following combination of characteristics:

(a) exhibits a compact mounding clump growth habit with the substantial absence of runners, (b) forms attractive white flowers on unbranched flower stalks, (c) forms lobed ovate green leaves having a matte finish during the summer that bear somewhat maroon centers and turn red of variable intensity during the fall, and (d) is particularly well suited for growing as a distinctive ornamental ground cover;

substantially as illustrated and described.

* * * * *